(12) United States Patent
Ikada et al.

(10) Patent No.: US 8,889,171 B2
(45) Date of Patent: Nov. 18, 2014

(54) TISSUE REGENERATION SUBSTRATE

(75) Inventors: Yoshito Ikada, Uji (JP); Shigehiko Suzuki, Kyoto (JP); Tsuguyoshi Taira, Ayabe (JP); Yoshitake Takahashi, Ayabe (JP); Kenji Tomihata, Ayabe (JP)

(73) Assignee: Gunze Limited, Ayabe-shi (JP)

( * ) Notice: Subject to any disclaimer, the term of this patent is extended or adjusted under 35 U.S.C. 154(b) by 1130 days.

(21) Appl. No.: 12/065,979

(22) PCT Filed: Sep. 5, 2006

(86) PCT No.: PCT/JP2006/317513
§ 371 (c)(1),
(2), (4) Date: Mar. 6, 2008

(87) PCT Pub. No.: WO2007/029677
PCT Pub. Date: Mar. 15, 2007

(65) Prior Publication Data
US 2009/0143287 A1 Jun. 4, 2009

(30) Foreign Application Priority Data
Sep. 9, 2005 (JP) ................... 2005-261840

(51) Int. Cl.
*A61L 27/34* (2006.01)
*A61L 27/26* (2006.01)
*A61L 27/58* (2006.01)
*A61L 27/56* (2006.01)
*A61L 27/60* (2006.01)
*A61L 27/54* (2006.01)

(52) U.S. Cl.
CPC ............... *A61L 27/54* (2013.01); *A61L 27/56* (2013.01); *A61L 2300/602* (2013.01); *A61L 2300/414* (2013.01); *A61L 27/60* (2013.01); *A61L 27/58* (2013.01); *A61L 27/26* (2013.01)
USPC ................... 424/426; 424/422; 424/484

(58) Field of Classification Search
IPC ........................... C07K 17/04,1/06
See application file for complete search history.

(56) References Cited

U.S. PATENT DOCUMENTS

| 5,618,312 | A | 4/1997 | Yui et al. |
| 6,262,332 | B1 | 7/2001 | Ketharanathan |
| 7,022,348 | B2 | 4/2006 | Ketharanathan |
| 2004/0235161 | A1 | 11/2004 | Tabata et al. |
| 2005/0004242 | A1 | 1/2005 | Sotome et al. |
| 2009/0312524 | A1* | 12/2009 | Lauritzen ............ 530/356 |

FOREIGN PATENT DOCUMENTS

| CN | 1149498 A | 5/1997 |
| CN | 1228338 A | 9/1999 |
| CN | 1228339 A | 9/1999 |
| CN | 1494439 A | 5/2004 |
| CN | 1575820 A | 2/2005 |
| CN | 1587391 A | 3/2005 |
| EP | 0568334 A1 | 11/1993 |
| JP | 11-047258 A | 2/1999 |
| JP | 11-319068 A | 11/1999 |
| JP | 2003-325652 A | 11/2003 |
| WO | WO 02/091955 A1 | 11/2002 |
| WO | WO 03-092759 A1 | 11/2003 |

OTHER PUBLICATIONS

Machine Translation of JP 11-047258 tranlated Jun. 10, 2010.*
International Search Report of PCT/JP2006/317513, date of mailing Oct. 3, 2006.
Kawai, K. et al.; "Accelerated tissue regeneration through incorporation of basic fibroblast growth factor-impregnated gelatin microspheres into artificial dermis"; Biomaterials , vol. 21, pp. 489-499 2000.
Tabata, Y. et al.; "Enhanced vascularization and tissue granulation by basic fibroblast growth factor impregnated in gelatin hydrogels"; Journal of Controlled Release, vol. 31, pp. 189-199, 1994.
Kimura, Y. et al..; "Adipose tissue engineering based on human preadipocytes combined with gelatin microspheres containing basic fibroblast growth factor"; Biomaterials, vol. 24, pp. 2513-2521, 2003.
Sasho, Y. et al; "Cell-preconfluent Baiyo Hifu eno Johosei bFGF Tenka Koka"; Japanese Journal of Burn Injuries, vol. 29, No. 1, pp. 24-30 2003.
Notification of First Office Action dated Aug. 26, 2010 from the Patent Office of the People's Republic of China for Patent No. 200680032611.8.
Doctoral Thesis, Zhejiang University "Construction of Collagen-Based Dermal Scaffolds for Tissue Engineering", 2004, 6 pages.(full English translation)(cited in Chinese Office Action dated Mar. 9, 2012, issued in corresponding Chinese Patent Application No. 200680032611.8).
Wissink et al., "Improved endothelialization of vascular grafts by local release of growth factor from heparinized collagen matrices", Journal of Controlled Release 64, (2000), pp. 103-114.(cited in Chinese Office Action dated Mar. 9, 2012, issued in corresponding Chinese Patent Application No. 200680032611.8).
Doctoral Thesis, Xiehe Medical University, China "Researches on Collagen-Based Tissue Engineering Scaffolds Materials", Jun. 2001, 7 pages.(full English translation)(cited in Chinese Office Action dated Mar. 9, 2012, issued in corresponding Chinese Patent Application No. 200680032611.8).
Yu Kimura et al.; "In vivo Adipose Tissue Regeneration by Biodegradable Scaffold with Different Compositions"; Polymer Preprints, Japan, vol. 54, No. 1, May 10, 2005, p. 2Pa171. w/partial English translation.(cited in Japanese Office Action dated Aug. 23, 2011).
Supplementary European Search Report dated Nov. 16, 2011, issued in corresponding European Patent Application No. 06797419.6.

* cited by examiner

*Primary Examiner* — Rebecca Prouty
(74) *Attorney, Agent, or Firm* — Westerman, Hattori, Daniels & Adrian, LLP

(57) ABSTRACT

The present invention provides a tissue regeneration substrate that has the ability to release a basic fibroblast growth factor (bFGF) and like cell growth factors in a sustained manner, into which cells can easily enter, and that is suitably used for regeneration of tissues. Specifically, the present invention provides a tissue regeneration substrate that comprises a cell growth factor adsorbed in a bioabsorbable porous substrate that contains collagen and gelatin, and a method for producing the same.

5 Claims, 6 Drawing Sheets ured skin, etc.
TISSUE REGENERATION SUBSTRATE

TECHNICAL FIELD

The present invention relates to a tissue regeneration substrate. Specifically, the present invention relates to an artificial dermis substrate, etc., for use in regenerating skin tissues on scalds/burns, injuries and like-acute skin defects; and decubiti, ulcers and like-chronic skin defects.

BACKGROUND ART

If a skin defect covers a wide area, the defect should be treated at an early stage. One method of regenerating skin to heal a defect involves artificial dermis tissues being regenerated in vivo by implanting a collagen sponge, which functions as a scaffold, in the body without seeding cells (this is referred to as an artificial dermis production method). The artificial dermis production method requires thin split-thickness skin grafting or transplantation of a cultured epidermis after regeneration of dermis-like tissues. In either case, regeneration of dermis components must be conducted as soon as possible.

A standard production method of artificial dermis involves obtainment of a collagen sponge by freeze-drying, and in order to control degradation and adsorption rates in vivo, a cross-linking treatment is usually conducted.

One method for promoting skin tissue regeneration involves applying a growth factor, such as a basic fibroblast growth factor (bFGF), to the skin surface. This method is somewhat effective because the applied growth factor can be adsorbed through the skin. However, the application has to be conducted every day in order to maintain the effect. Therefore, several attempts have been made to find a method of maintaining the effect with only a one-time administration by sustainedly releasing the growth factors.

For example, Kawai et al., discloses that by infusing a bFGF-impregnated gelatin microsphere into an artificial dermis, a sustained release of bFGF and construction of skin tissues in vivo can be promoted (Non-Patent Document 1). Additionally, when a cell seeded-type cultured skin is prepared, constitution of tissues is promoted by adding a bFGF-impregnated gelatin microsphere (Non-Patent Document 2).

However, such methods require impregnating bFGF in a microsphere, and further infusing the thus-prepared microsphere into an artificial dermis at a clinical site, resulting in a complicated operation.

If it is possible to impart the artificial dermis itself with the ability to release a growth factor in a sustained manner, the only procedure necessary at a clinical site is to apply a growth factor to the artificial dermis, greatly simplifying the process.

The cell growth factor most widely used in current clinical fields is basic fibroblast growth factor (bFGF). The bFGF has an isoelectric point of 9.6 and can adhere to a gelatin having an isoelectric point of, for example, 5.0, by electrical interaction. By utilizing such characteristics, it is possible to release bFGF in vivo in a sustained manner with time by using a bFGF-adsorbed microsphere, which can be prepared by impregnating a microsphere made of acid gelatin (having an isoelectric point of 5.0) with b FGB (Patent Document 1, and Non-Patent Document 3).

However, this method requires manipulation, for example, making the bFGF to be adsorbed in a particulate microsphere, and then infusing the thus-obtained bFGF-adsorbed microsphere into a substrate. This makes the method complicated and hard to use in a clinical site.

If an artificial dermis material is prepared by making the bFGF to be adsorbed in an acid gelatin, in which a bFGF is easily adsorbed, a substrate having a sustained releasing ability may be obtained. However, gelatin is inferior to collagen in vivo in terms of ease of cell infiltration, etc., and therefore it is not suitable for tissue regeneration. Accordingly, a substrate that can adsorb an adequate amount of bFGF and to which surrounding cells can easily enter is demanded.

Patent Document 2 discloses a medical device that contains gelatin and collagen as essential components, and is irradiated with ultraviolet to achieve cross-linking. The medical substrate is suitably used as a cell culturing carrier, for cultured skin, etc.

Patent Document 1: Japanese Unexamined Patent Publication No. 2003-325652
Patent Document 2: Japanese Unexamined Patent Publication No. 1999-47258
Non-patent Document 1: K. Kawai et al., Biomaterials, Vol. 21, pp. 489-499 (2000)
Non-patent Document 2: Saso et al., Japanese Journal of Burn Injuries, Vol. 29, pp. 24-30
Non-patent Document 3: Y. Tabata et al., J. Controlled release, Vol. 31, pp. 189-199 (1994)

DISCLOSURE OF THE INVENTION

Problem to be Solved by the Invention

An object of the present invention is to provide a tissue regeneration substrate that has the ability to release a basic fibroblast growth factor (bFGF) and like cell growth factors in a sustained manner, into which cells can easily enter, and that is suitably used for regeneration of tissues.

Means for Solving the Problem

The present inventors conducted extensive research to solve the above problems and found that a substrate, which is obtained by making a bioabsorbable porous substrate that contains collagen and gelatin to adsorb bFGF, is suitably usable as a tissue regeneration substrate for regenerating skin tissues, because the substrate exhibits an excellent ability to release bFGF in a sustained manner, and the substrate allows cells to easily enter therein. The present invention has been accomplished based on this finding and further study.

Specifically, the present invention provides the tissue regeneration substrates and the production processes as below:

Item 1. A tissue regeneration substrate comprising a bioabsorbable porous substrate that contains collagen and gelatin, the bioabsorbable porous substrate having a cell growth factor therein.

Item 2. A tissue regeneration substrate according to Item 1, wherein the content of the gelatin in the bioabsorbable porous substrate is 1 to 70 wt. %.

Item 3. A tissue regeneration substrate according to Item 1 or 2, wherein the cell growth factor is a basic fibroblast growth factor (bFGF).

Item 4. A tissue regeneration substrate according to any one of Items 1 to 3, wherein the amount of the cell growth factor released to phosphate buffer saline (PBS) after being dipped in the PBS at 37° C. for three days is not greater than 7 wt. % of the total amount of cell growth factor initially contained in the tissue regeneration substrate.

Item 5. A tissue regeneration substrate according to any one of Items 1 to 4, wherein the amount of the cell growth factor released to phosphate buffer saline (PBS) after being dipped in the PBS at 37° C. for three days is not greater than 15 wt. % of the total amount of cell growth factor initially contained in the tissue regeneration substrate.

Item 6. A tissue regeneration substrate according to any one of Items 1 to 5, which has pores with interconnected structure having an average pore diameter of 10 to 500 μm.

Item 7. A tissue regeneration substrate according to any one of Items 1 to 6, which is degraded and absorbed in vivo within three weeks.

Item 8. A method for producing a tissue regeneration substrate comprising the steps of:

freeze-drying an aqueous mixture containing collagen and gelatin;

subjecting the thus-obtained freeze-dried substance to cross-linking; and making the cross-linked substance to contain a cell growth factor.

The present invention is explained in detail below.

I. Tissue Regeneration Substrate

The tissue regeneration substrate of the present invention comprises a cell growth factor in a collagen- and gelatin-containing bioabsorbable porous substrate. The tissue regeneration substrate of the present invention is a substrate used in tissue engineering, for example, a substrate for use in regenerating skin, bone, cartilage, myocardium, and/or fat. In particular, it is suitably used as a tissue regeneration substrate for skin (dermis), i.e., an artificial dermis substrate.

The bioabsorbable porous substrate used as the tissue regeneration substrate of the present invention contains collagen and gelatin as essential components.

There is no limitation to the gelatin, and usable examples include those derive from bone, tendon, skin, etc. of cattle, swine, chicken, salmon, and the like. It is preferable that the gelatin have been subjected to an acid treatment or alkali treatment. Acid-treated gelatin has a positive charge, while alkali-treated gelatin has a negative charge. Utilizing these electrical charges, various types of cell growth factors can be electrostatically immobilized, without denaturation, on a gelatin-containing bioabsorbable porous substrate with a positive or negative electrical charge. This achieves a desirable sustained release of cell growth factors (for example, bFGF).

There is no limitation to the collagen, and usable examples include those derived from skin, tendon, etc. of bovine, pig, etc. In order to eliminate antigenicity and improve safety, atelocollagen, which is obtained by treating collagen with protease, pepsin and like enzymes to eliminate telopeptide as much as possible, is preferable. Atelocollagen can be categorized into I to IV types, and can be selected depending on the usage of the substrate. When the substrate is used for cultured skin or wound dressing, type I or III is preferable, as they have constituent components similar to those of dermis. By making a bioabsorbable porous substrate to contain collagen, cells can easily enter the substrate.

The content of the gelatin in the bioabsorbable porous substrate is generally about 1 wt. % to about 70 wt. %, preferably about 20 wt. % to about 60 wt. %, and more preferably about 30 wt. % to 50 wt. %. If the gelatin content is unduly large, it is difficult for surrounding tissues to enter the bioabsorbable porous substrate. In contrast, if the gelatin content is unduly small, sufficient sustained releasing ability cannot be obtained since the adhesion between the gelatin and cell growth factors by electrostatic interaction becomes weak. If the gelatin content falls within the above range, the abilities of gelatin and collagen can be fully exploited, and a large therapeutic effect can be attained.

Because the bioabsorbable porous substrate functions as a substrate for three-dimensionally regenerating tissues, it is preferable that the bioabsorbable porous substrate have a porous structure, and having many interconnected pores (continuous small pores) is particularly preferable. By employing such a structure, when cells are seeded in the tissue regeneration substrate of the present invention, the cells can enter and adhere to the small pores and extend three-dimensionally; and when the substrate is implanted without seeding cells therein, surrounding cells can easily enter the substrate. Furthermore, this structure makes it possible to supply sufficient nutrition to the adherent cells and proliferate and differentiate the cells normally.

The average pore diameter of the small pores in the bioabsorbable porous substrate can be suitably selected depending on the tissue or organ to be regenerated, but is preferably about 10 μm to about 500 μm, and more preferably about 50 μm to about 300 μm. If the average pore diameter is smaller than 10 μm, cellular adhesiveness may be remarkably decreased, since cells cannot enter the bioabsorbable porous substrate, or adherent cells may not be able to extend three-dimensionally. If the average pore diameter exceeds 500 μm, the cell density becomes too low, and tissues or organs may not be able to regenerate.

The porous structure of the above-mentioned bioabsorbable porous substrate is directly inherited to the tissue regeneration substrate of the present invention.

The tissue regeneration substrate of the present invention comprises cell growth factors in a collagen- and gelatin-containing bioabsorbable porous substrate. There is no limitation to the cell growth factors as long as they can promote vascularization and enhance the activity of cells. Examples thereof include cell growth factors having a vascularization action, such as a basic fibroblast growth factor (bFGF), an acid fibroblast growth factor (aFGF), a vascular endothelial cell growth factor (VEGF), a hepatocyte growth factor (HGF), a plasma-derived growth factor (PDGF), angiopoietin, and a transforming growth factor (TGF). The preferable embodiment of the present invention is bFGF.

There is no limitation to the content of the cell growth factor in the tissue regeneration substrate of the present invention and can be suitably selected depending on the tissues and the like to be regenerated. Preferably it falls within the range of from about 0.1 μg to about 100 μg, and more preferably from about 1 μg to about 50 μg per 1 $m^2$ of the substrate.

The tissue regeneration substrate of the present invention has an excellent ability to stably release cell growth factors in a sustained manner over a long time period. For example, bFGF promotes vascularization and enhances the activity of cells, but it is unstable in vivo and cannot achieve the expected biological effects when used in an aqueous solution. However, when the above-mentioned bioabsorbable porous substrate contains a predetermined amount of bFGF, the action of the bFGF can be stably maintained by releasing it in a sustained manner.

The tissue regeneration substrate of the present invention has a distinctive feature, for example, the amount of the cell growth factor released to phosphate buffer saline (PBS) after dipping in the PBS at 37° C. for three days is not greater than 7 wt. % of the total amount of cell growth factor initially contained in the tissue regeneration substrate (preferably not greater than 6 wt. %). The amount of the cell growth factor released to PBS after being dipped in the PBS at 37° C. for seven days is not greater than 15 wt. % of the total amount of cell growth factor initially contained in the tissue regeneration substrate (preferably not greater than 13 wt. %). In particular, when the cell growth factor is bFGF, the above-mentioned sustained releasing ability can be attained with sufficient reproducibility.

Furthermore, because the tissue regeneration substrate of the present invention comprises a bioabsorbable substrate containing collagen and gelatin, it can be degraded and adsorbed in vivo within three weeks.

The lower limit of the water content of the tissue regeneration substrate is preferably 90%, and the upper limit thereof is preferably 99.8%. The water content of the bioabsorbable porous substrate depends on the degree of cross-linkage of the bioabsorbable porous substrate. The higher the degree of cross-linkage, the lower the water content. If the water content is less than 90%, the tissue regeneration substrate may not have sufficient flexibility to be used in implantation. However, if the water content exceeds 99.8%, the obtained tissue regeneration substrate may not be able to maintain sufficient strength in a culture solution or buffer. More preferably, the lower limit of the water content is 95%, and the upper limit thereof is 98%. The water content can be obtained in the formula below.

Water content(%)=[($W_s$−$W_d$)/$W_s$]×100(%), wherein, Ws indicates the weight (on a wet basis) of the tissue regeneration substrate dipped in a phosphate buffered saline at 25° C. for one hour, and Wd indicates the weight (on a dry basis) of the substrate after being completely dried using a vacuum dryer.

II. Method for Producing Tissue Regeneration Substrate

The tissue regeneration substrate of the present invention is produced by the procedure comprising the steps of freeze-drying an aqueous mixture that contains collagen and gelatin; cross-linking the thus-obtained dried substance; and putting a cell growth factor into the cross-linked substance.

First, the above-mentioned gelatin and collagen are mixed to obtain an aqueous solution. The aqueous solution is flow cast in an appropriate mold, and then frozen at −40° C. to −80° C. for about 30 minutes to about 2 hours. This frozen substance is then subjected to freeze-drying, after which a spongy bioabsorbable porous substrate is obtained.

Second, the thus-obtained freeze-dried substance is subjected to a cross-linkage treatment to obtain a bioabsorbable porous substrate. There is no limitation to the method for cross-linking the freeze-dried substance, and examples thereof include heat cross-linking method, gamma-ray irradiation method, ultraviolet irradiation method, electron beam irradiation method, X-ray irradiation method, chemical cross-linking method using a cross-linking agent, etc. Among these, chemical cross-linking method using a cross-linking agent is particularly preferable, in order to attain a uniform degree of cross-linkage through the entire substrate.

The chemical cross-linking method can be specifically conducted by, for example, immersing the freeze-dried substance in a solution that contains glutaraldehyde or like cross-linking agent. Excessive glutaraldehyde is removed by washing with water, and conducting further freeze-drying, if necessary, thereby obtaining a cross-linked bioabsorbable porous substrate.

Subsequently, a cell growth factor is added to the obtained cross-linked substrate. There is no limitation to the method thereof, and, for example, an aqueous solution that contains a cell growth factor may be added dropwise to the cross-linked substrate; the cross-linked substrate may be impregnated with an aqueous solution that contains a cell growth factor; etc. Thereafter, an additional drying step may be conducted, if necessary.

Effect of the Invention

The tissue regeneration substrate of the present invention (in particular, artificial dermis substrate) can stably release cell growth factor in a sustained manner. Furthermore, since the cells can be easily infiltrated, wound healing can be accelerated and treatment time can be remarkably shortened.

BEST MODE FOR CARRYING OUT THE INVENTION

The present invention is explained in detail below with reference to Examples, but the scope of the present invention is not limited to these.

Test Example 1

(1) Production of Mixed Sponge of Collagen and Gelatin

Swine tendon-derived I-type collagen and swine skin-derived gelatin were mixed to obtain an aqueous solution. The aqueous solution was placed in a mold and frozen at −40° C. for one hour and then freeze-dried, obtaining a sponge.

Heat cross-linkage was performed by processing this sponge at 110° C. under a vacuum. After the heat cross-linkage, the sponge was dipped in an aqueous solution of 0.2% glutaraldehyde and 0.05 N acetic acid to conduct chemical cross-linkage. Excessive glutaraldehyde was removed by washing with water, and conducting further freeze-drying, obtaining a cross-linked collagen-gelatin sponge. The thus-obtained cross-linked sponge was used in the in vitro sustained releasing experiment conducted as the next step.

(2) In Vitro Sustained Releasing Experiment

The sponge used in the experiment had a gelatin content of 0, 10, 30, or 50 wt. %. Each of these sponges was formed into a shape having a diameter of 12 mm and a thickness of 3 mm. An aqueous solution of bFGF (100 μl) was added to the sponge dropwise so that 40 μg of bFGF was impregnated therein.

The sustained releasing experiment was conducted in such a manner that each of the sponge was dipped in the PBS at 37° C., and the amount of bFGF released into PBS was evaluated by ELISA 1, 3, 5, 7, and 9 days after the initiation of the impregnation.

Figure 1:
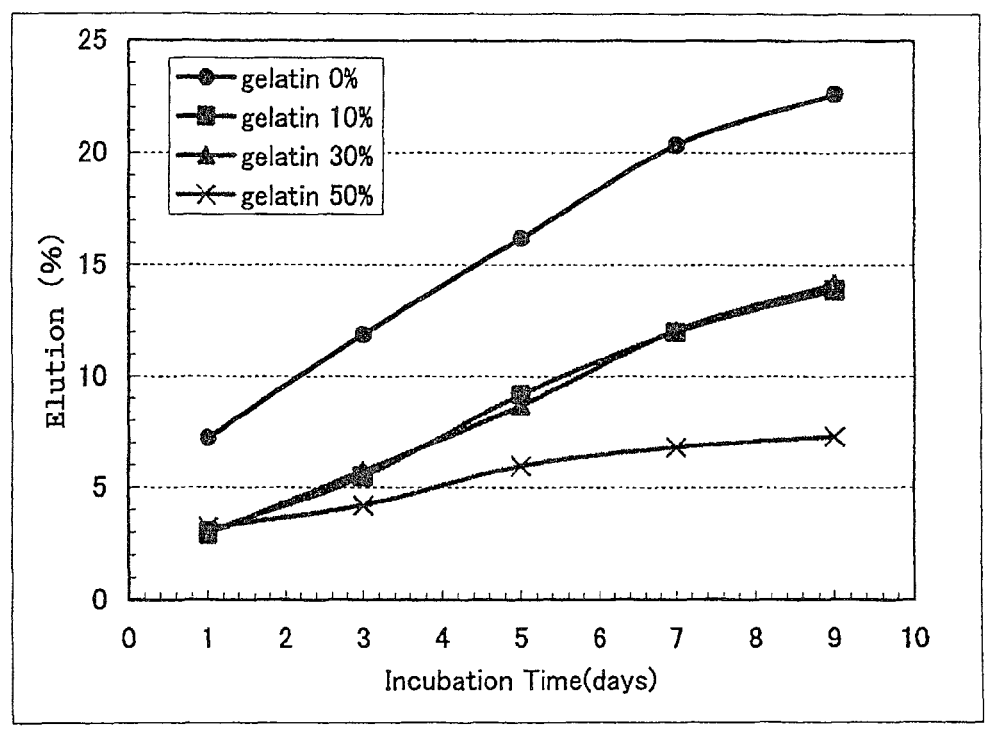
FIG. 1 is a graph showing the results of Test Example 1, wherein sustained releasing of bFGF in vitro was examined.
Figure 2:
FIG. 2 shows an image of a piece of tissue when the gelatin content of the sponge in Test Example 1 is 0 wt. %.
Figure 3:
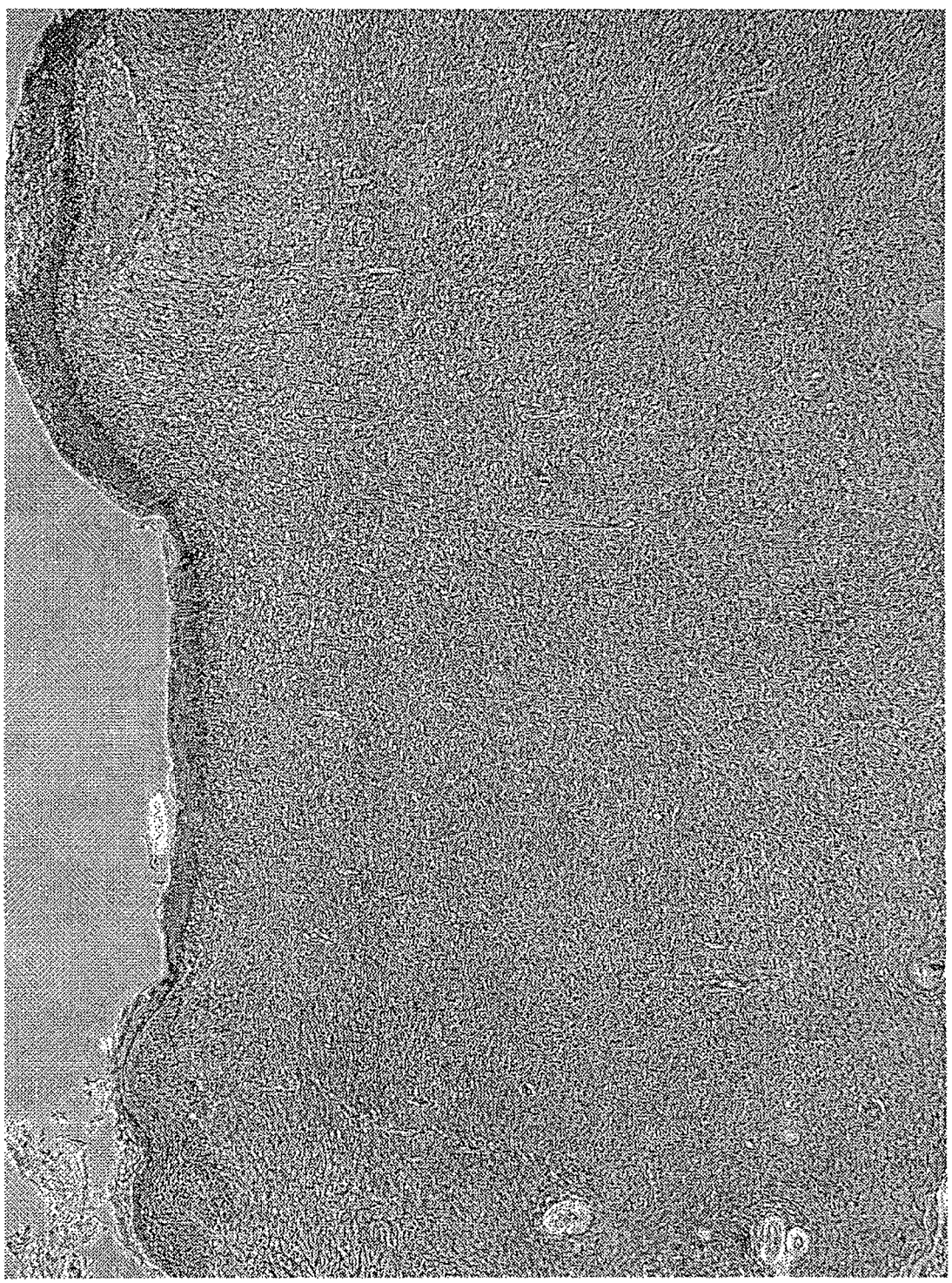
FIG. 3 shows an image of a piece of tissue when the gelatin content of the sponge in Test Example 1 is 10 wt. %.
Figure 4:
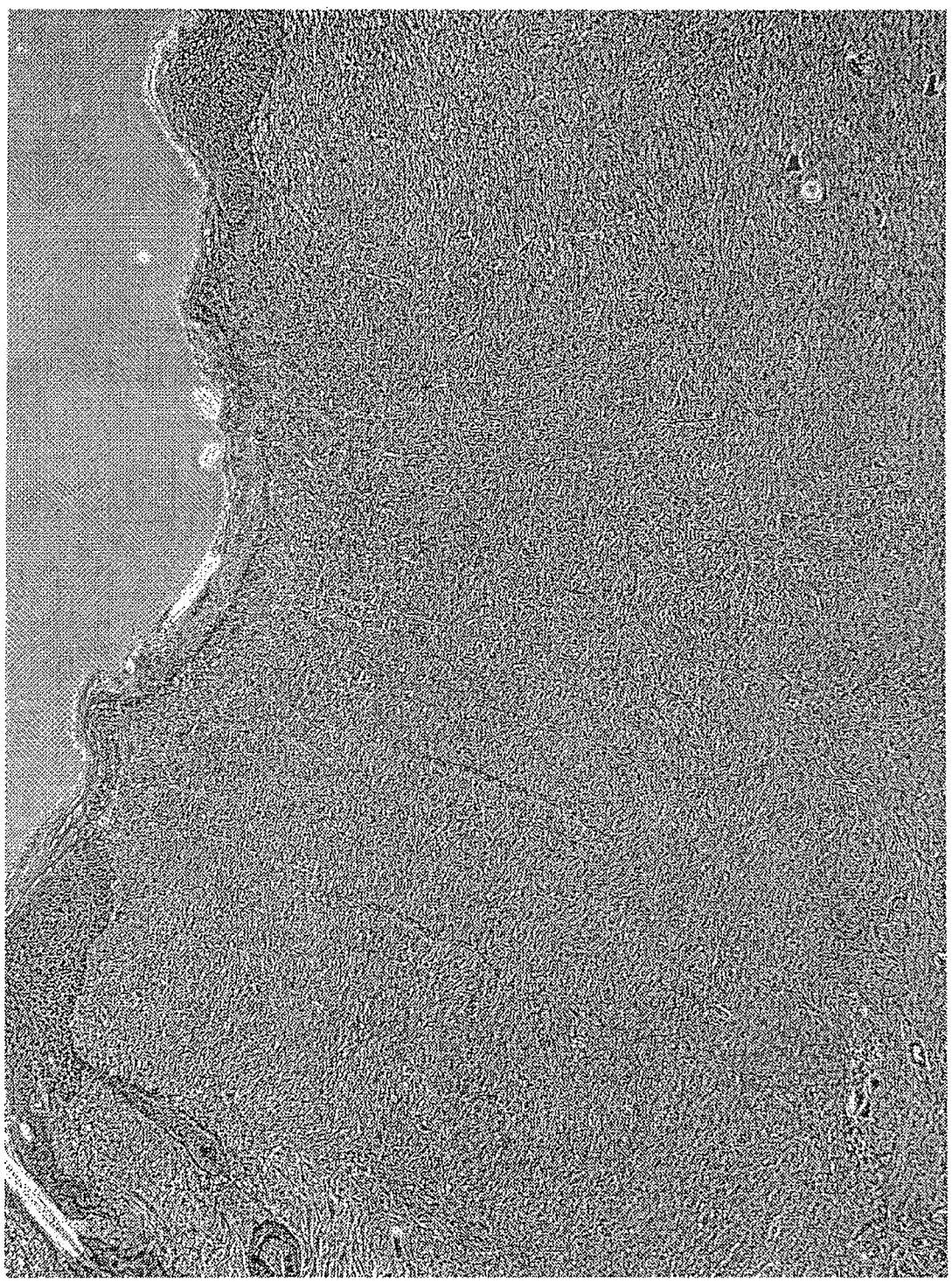
FIG. 4 shows an image of a piece of tissue when the gelatin content of the sponge in Test Example 1 is 30 wt. %.
Figure 5:
FIG. 5 shows an image of a piece of tissue when the gelatin content of the sponge in Test Example 1 is 50 wt. %.
Figure 6:
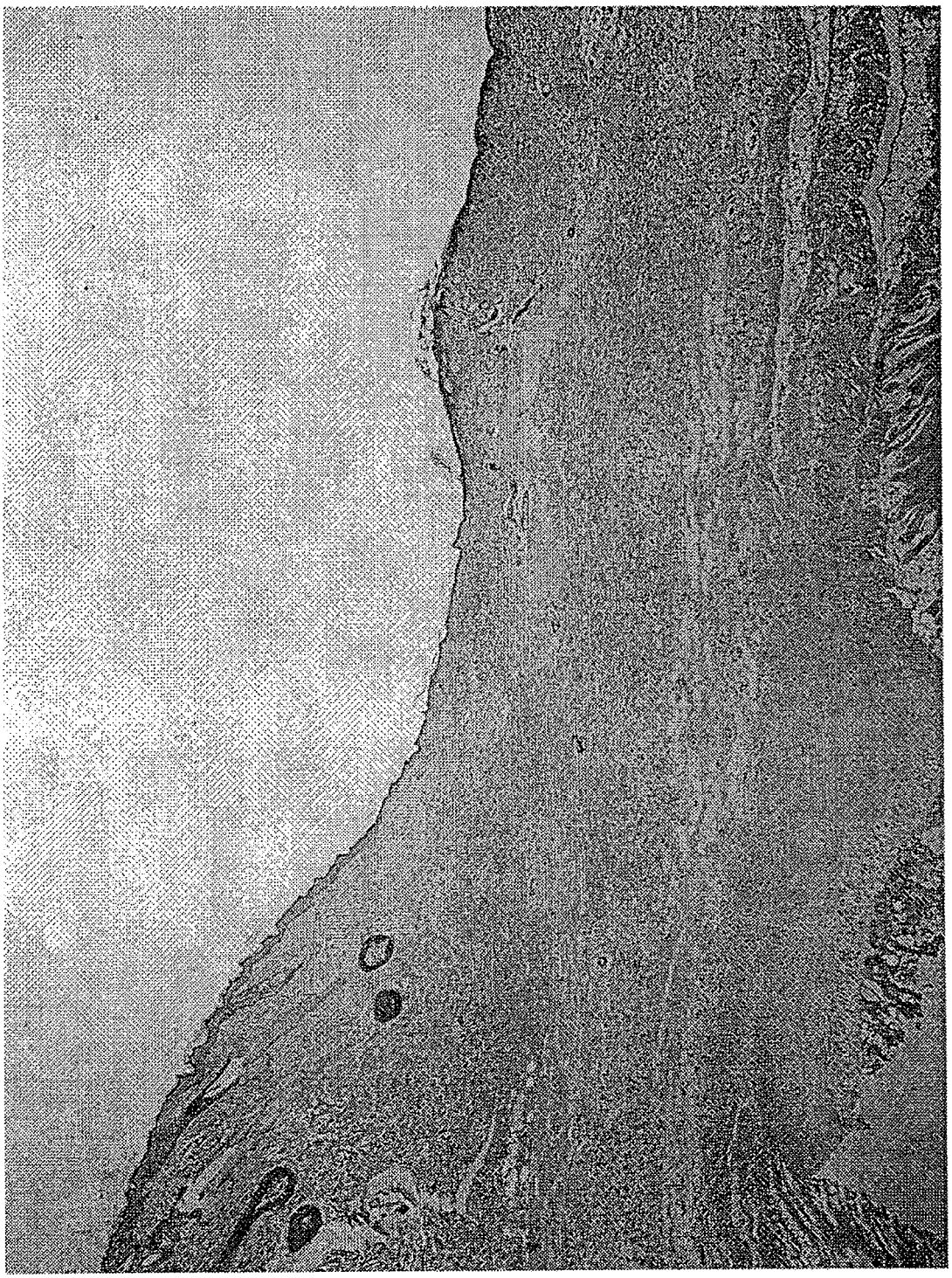
FIG. 6 shows an image of a piece of tissue when the gelatin content of the sponge in Test Example 1 is 100 wt. %.

Table 1 and FIG. 1 show the change of the bFGF release rate with the passage of time when the weight of the bFGF contained in each sponge immediately after the immersion was determined as 100, i.e., bFGF elution rate (%).

TABLE 1

| days | Gelatin content (wt %) | | | |
| --- | --- | --- | --- | --- |
| | 0 | 10 | 30 | 50 |
| 1 | 7.2 | 3.0 | 2.9 | 3.2 |
| 3 | 11.9 | 5.5 | 5.7 | 4.2 |
| 5 | 16.2 | 9.2 | 8.7 | 6.0 |
| 7 | 20.3 | 12.0 | 12.1 | 6.8 |
| 9 | 22.6 | 13.9 | 14.2 | 7.3 |

(3) Implantation Test

The sponge used in the experiment had a gelatin content of 0, 10, 30, 50, or 100 wt. %. Each of these sponges was formed into a shape having a diameter of 12 mm and a thickness of 3 mm. An aqueous solution of bFGF (100 μl) was added dropwise to the sponge so that 40 μg of bFGF was impregnated therein. This sponge was implanted in the full-thickness skin defect in the back of a guinea pig. FIGS. 2 to 6 show images of tissue pieces after the implantation.

In the sponge having a gelatin content of 100 wt. %, little infiltration of surrounding tissues into cells was observed, and an image of downgrowth, i.e., cells getting under the sponge, was also observed. The higher the collagen content, the more infiltration of cells and excellent regeneration of tissues would be observed. However, when collagen content was 100 wt. %, the sustained releasing ability of cell growth factors was reduced. In order to exhibit sufficient cell growth factor sustained releasing ability, without preventing the infiltration of surrounding tissues, having an appropriate gelatin content is essential.

The invention claimed is:

1. A tissue regeneration substrate, comprising:
a bioabsorbable porous substrate that contains collagen and alkali-treated gelatin, the bioabsorbable porous substrate being chemically cross-linked and having a basic fibroblast growth factor (bFGF) therein,
wherein the content of the alkali-treated gelatin in the bioabsorbable porous substrate is about 10 wt. %,
wherein the tissue regeneration substrate has small pores with an average pore diameter of about 10 μm to about 500 μm,
wherein the amount of the bFGF released to phosphate buffer saline (PBS) after being dipped in the PBS at 37° C. for three days is not greater than 7 wt. % of the total amount of the bFGF initially contained in the tissue regeneration substrate, and
wherein the amount of the bFGF released to phosphate buffer saline (PBS) after being dipped in the PBS at 37° C. for seven days is not greater than 15 wt. % of the total amount of the bFGF initially contained in the tissue regeneration substrate.

2. A tissue regeneration substrate according to claim 1, wherein small pores in said tissue regeneration substrate have an interconnected structure.

3. A tissue regeneration substrate according to claim 1, wherein said tissue regeneration substrate is degraded and absorbed in vivo within three weeks.

4. A method for producing a tissue regeneration substrate having small pores with an average pore diameter of about 10 μm to about 500 μm, comprising:
freeze-drying an aqueous mixture containing collagen and alkali-treated gelatin to obtain a bioabsorbable porous substrate, the content of the alkali-treated gelatin in the bioabsorbable porous substrate being about 10 wt. %;
subjecting the thus-obtained freeze-dried bioabsorbable porous substrate to chemical cross-linking; and
adding a basic fibroblast growth factor (bFGF) to the cross-linked substrate.

5. A tissue regeneration substrate according to claim 1, wherein the content of the bFGF in the tissue regeneration substrate falls within the range of from about 0.1 μg to about 100 μg per 1 m$^2$ of the substrate.

* * * * *